(12) United States Patent
Seabrook et al.

(10) Patent No.: US 7,144,487 B2
(45) Date of Patent: Dec. 5, 2006

(54) FACTOR VIII SEPARATION

(75) Inventors: Elizabeth Jean Seabrook, Lane Cove (AU); Thomas Norman Turton, Lane Cove (AU); Brendon Conlan, Tarrytown, NY (US)

(73) Assignee: Life Therapeutics, Inc., Frenchs Forest (AU)

( * ) Notice: Subject to any disclaimer, the term of this patent is extended or adjusted under 35 U.S.C. 154(b) by 444 days.

(21) Appl. No.: 10/196,435

(22) Filed: Jul. 15, 2002

(65) Prior Publication Data

US 2003/0106798 A1 Jun. 12, 2003

(30) Foreign Application Priority Data

Jul. 13, 2001 (AU) .................................... PR6388

(51) Int. Cl.
*B01D 57/02* (2006.01)
(52) U.S. Cl. ...................... 204/543; 204/450; 204/518; 204/600; 204/627
(58) Field of Classification Search ........ 204/518–544, 204/627–640
See application file for complete search history.

(56) References Cited

U.S. PATENT DOCUMENTS

| 4,250,008 | A | * | 2/1981 | Mattock | ...................... | 204/545 |
| 4,382,028 | A | * | 5/1983 | Paget | ......................... | 530/364 |
| 4,446,134 | A | * | 5/1984 | Naito et al. | ..................... | 514/2 |
| 5,039,386 | A | * | 8/1991 | Margolis | .................... | 204/466 |
| 6,270,672 | B1 | * | 8/2001 | Turecek et al. | ............. | 210/645 |

FOREIGN PATENT DOCUMENTS

| GB | 2096174 | 10/1982 |
| WO | WO 79/00299 | 5/1979 |

OTHER PUBLICATIONS

Fatouros, A. et al., "Recombinant Factor VIII SQ—Inactivation Kinetics in Aqueous Solution and the Influence of Disaccharides and Sugar Alcohols" Pharm. Res. 14, 1679-1684. (1997).*

Balague, C. et al., "Sustained high-level expression of full-length human factor VIII and restoration of clotting activity in hemophilic mice using a minimal adenovirus vector" Blood. 95 (3) 820-828. (2000).*

Wikipedia entry for albumin, from "Albumin: Definition and Much More From Answers.com", available at http://www.answers.com/albumin. Dec. 2005, 1 page.*

Medline abstract Accession No. 83173756 (PubMed ID:6404060) & Austen DE, Carwritght T, Dickerson CH, "Partial separation of blood clotting factors, albumin, and IgG by continuous free film electrophoresis" Vox Sanguinis, (Mar. 1983), 44 (3), 151-5. Abstract.

Medline abstract Accession No. 82046802 (PubMed ID: 6794637) & Perret BA, et al., "Fractionation of individual, biologically active Factor VIII multimers", Biochimica et Biophysica ACTA, Jun. 29, 1981, 669 (1), 98-104. Abstract.

Bidwell E., et al., "Experiments with Factor VIII separated from fibrinogen by electrophoresis in free buffer film", Chemical Abstract Accession No. 65:91977, Brit. J. Kaematol, 1996, 12 (5), 583-94. Abstract.

* cited by examiner

*Primary Examiner*—Nam Nguyen
*Assistant Examiner*—Jeffrey Barton
(74) *Attorney, Agent, or Firm*—Cooley Godward Kronish LLP

(57) ABSTRACT

The claims describe methods for isolating functionally active Factor VIII using a membrane-based separation system containing a separation membrane to create a first and second interstitial volume between at least two restriction membranes. One or more stabilizing agents are added to the sample and/or an interstitial volume. A solvent in the first interstitial volume maintains FVIII in a desired charge state. Applying a potential between the first and second interstitial volumes separates FVIII on one side of the separation membrane from unwanted molecules on the other side of the separation membrane. These methods may also be used as a substitute for one or more steps in a conventional purification scheme for the separation of native or recombinant FVIII.

22 Claims, 9 Drawing Sheets

Lane 1: MW Marker
Lane 2: S1 0 (Cell Supernatant)
Lane 3: S1 0 (Cell Sup'n + FVIII)
Lane 4: S1 30
Lane 5: S1 60
Lane 6: S2 0
Lane 7: S2 30
Lane 8: S2 60
Lane 9: MW Marker

FACTOR VIII SEPARATION

CROSS-REFERENCE TO RELATED APPLICATIONS

This application claims benefit of the Australian Provisional Application No. PR 6388 filed Jul. 13, 2001.

FIELD

The present application relates to methods and apparatus for the separation of clotting factors from blood or recombinant sources, particularly separation of Factor VIII from plasma.

BACKGROUND

Human Factor VIII (FVIII) is a 265 kDa glycoprotein which circulates in plasma (0.1 μg/mL) bound to von Willebrand factor (vWf). The glycoprotein is highly sensitive to proteolytic processing which brings about both its activation and destruction, therefore regulating its role as a co-factor in the coagulation cascade (blood clotting). Activated FVIII (FVIIIa) is a co-factor in the activation of Factor X to Factor Xa. A deficiency in FVIII may lead to the bleeding disorder Haemophilia A.

The average industrial yield of FVIII from plasma is 140 to 270 international units (IU) per litre of plasma (1 IU is the average amount of FVIII activity found in 1 mL of pooled plasma=0.2 μg). The first step of FVIII conventional purification is typically cryoprecipitation (traditional Cohn fractionation) which yields 40–50% of FVIII. The cryoprecipitate containing the FVIII is then treated using chromatography, typically immunoaffinity and ion exchange. Minimizing the loss of FVIII at each of the processing steps is desired to improve yield since current supply of suitable FVIII is inadequate. Hemasure Denmark A/S has developed technology in an attempt to combat current problems with traditional Cohn fractionation of plasma. Hemasure uses a high capacity gel filtration step to replace the initial cryoprecipitation step reported to provide a step yield of 60–70% FVIII with a total process yield of 200 IU of FVIII/litre plasma. J. Dam, *Downstream*, vol. 31, p. 65 (Dec. 1999). Although this method results in an improved yield, there are still significant losses of FVIII in the process. Recombinant production is another source of FVIII, but this source has not replaced FVIII obtained from natural sources. Current purification schemes are time consuming, result in a significant loss of FVIII, and do not adequately remove pathogens, particularly viruses, without adversely affecting FVIII activity or yield.

It has been reported that several thousand different proteins coexist in plasma. Obtaining a given protein from such a complex mixture can be difficult, especially if the given protein must retain its biological activity in its isolated state. Currently, it is very difficult to purify or separate FVIII in reasonable quantities with good yields from plasma. As an example, for plasma having an average protein concentration of 70 mg/mL, FVIII (~0.1 μg/mL) constitutes approximately only 0.00014% of total plasma protein. The presence of FVIII in such low concentrations in plasma or recombinant sources usually requires large amounts of plasma or other sources to obtain reasonable commercial yields. Hence, production costs are increased and typically require process step reduction.

FVIII is a relatively unstable protein in plasma. As a result, standard purification technology applied to FVIII separation has difficulty obtaining a method for obtaining large amounts of biologically active FVIII. Current processes involve stabilizing the FVIII preparation at the end of the purification scheme with stabilizing agents, the most common being human albumin. However, addition at the end of the purification process may be too late to protect the activity of the separated FVIII. "Kogenate-F", a recombinant FVIII (rFVIII) therapeutic product formulated with sucrose, may eliminate the need to add human albumin to the preparation.

Viral contamination of FVIII preparations is also a potential problem. Typically, solvent detergent (SD), pasteurization, Methylene Blue (MB) and UV treatment or a combination thereof are used to inactivate viruses in FVIII preparations. However, traditional viral removal steps often result in loss or inactivation of FVIII.

SUMMARY

The present application relates to various methods and apparatus for isolating functionally active Factor VIII using a membrane-based electrophoresis separation system.

In one aspect, these methods use an electrophoresis apparatus containing a separation membrane to create a first and second interstitial volume between at least two restriction membranes. One or more stabilizing agents are added to the sample and/or an interstitial volume. A solvent in the first interstitial volume maintains FVIII in a desired charge state. Applying a potential between the first and second interstitial volumes separates FVIII on one side of the separation membrane from unwanted molecules on the other side of the separation membrane.

These and other features of the claims will be appreciated from review of the following detailed description of the application along with the accompanying figures.

DETAILED DESCRIPTION

Preferred embodiments of isolating functionally active Factor VIII using a membrane-based electrophoresis separation system according to the in a conventional purification scheme for the separation of native FVIII or rFVIII.

Figure 1:
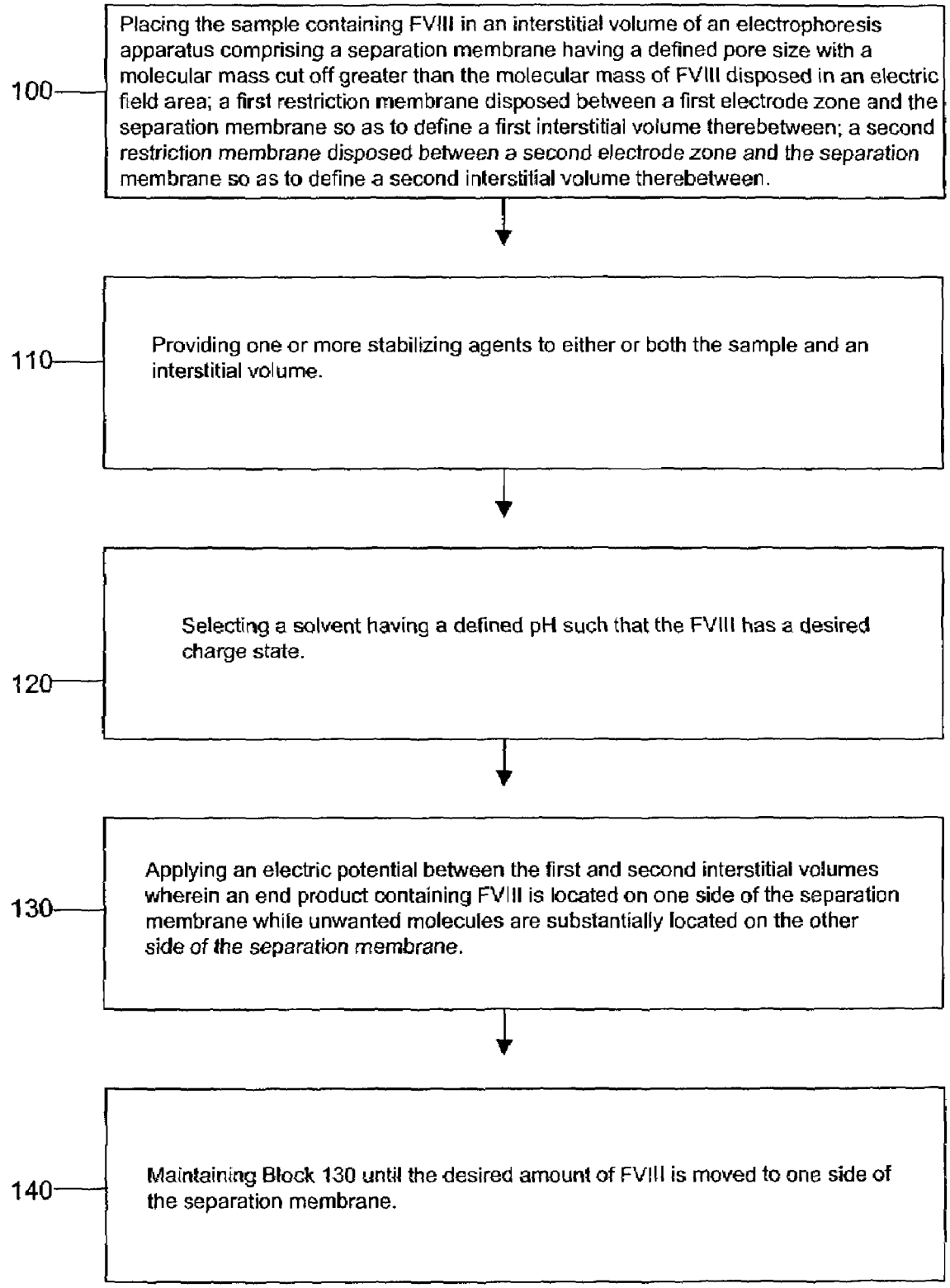
FIG. 1 is a block diagram of a method for isolating functionally active Factor VIII using a membrane-based electrophoresis separation system.

FIG. 1 refers of a block diagram of a method of obtaining FVIII from a sample in accordance with one aspect of the present inventions. In one embodiment, the sample can be plasma or a fraction thereof, cryoprecipitate or a fraction thereof, a source of recombinant FVIII, or combinations or mixtures thereof. In another embodiment, the sample can be cell supernatant or cell lysate containing a recombinant (rFVIII). However, other samples containing FVIII that are amenable to membrane-based electrophoresis may be used according to the present methods.

Block 100 depicts placing a sample containing FVIII in an interstitial volume of an electrophoresis apparatus. A suitable electrophoresis apparatus contains a separation membrane having a defined pore size with a molecular mass cut off different from the molecular mass of FVIII. The separation membrane may be an electrophoresis separation membrane having a defined molecular mass cut off. For example, the molecular mass cut off may be greater than the molecular mass of FVIII or the cut off or may be lower than the molecular mass of FVIII. In one embodiment, the electrophoresis separation membrane has a molecular mass cut off from about 1 kDa to about 2000 kDa. However, those skilled in the art will appreciate that other molecular mass cut offs may be used depending on the molecular masses of other molecules in the sample, such as contaminants, salts, or stabilizing agents. In one embodiment, the separation membrane is comprised of polyacrylamide. It will be appreciated, however, that other membrane chemistries or constituents can be used. The separation membrane is located in an electric field area.

A restriction membrane disposed between a first electrode zone and the separation membrane defines a first interstitial volume therebetween. A second restriction membrane disposed between a second electrode zone and the separation membrane defines a second interstitial volume therebetween. For convenience only, the first interstitial volume or stream is called stream 1 (S1) and the second interstitial volume or stream is called stream 2 (S2).

In one embodiment, the restriction membranes forming the first and second interstitial volumes are provided as a cartridge or cassette positioned between the electrode zones of the apparatus. In another embodiment, the configuration of the cartridge is preferably a housing with the separation membrane positioned between the first and second restriction membranes thus forming the required interstitial volumes. In some embodiments, the cartridge or cassette is removable from an electrophoresis apparatus adapted to contain or receive the cartridge. Other membrane configurations containing a separation membrane and restriction membranes to form the interstitial volumes are also contemplated by the present claims.

In one embodiment, the first and second restriction membranes are formed from polyacrylamide. However, other membrane chemistries may be used to form suitable restriction membranes and are known in the art. Typically, the restriction membranes have molecular mass cut offs less than the separation membrane. In some embodiments, the restriction membranes have molecular mass cut off between 1 kDa to about 1000 kDa. However, other mass cut offs may be used. The selection of the molecular mass cut off of the restriction membranes will depend on the sample being processed and the size of the macromolecules to be removed. The restriction membranes may have the same molecular mass cut off or different cut offs, forming an asymmetrical arrangement.

One embodiment employs an electrophoresis apparatus that contains a cathode in a cathode zone, an anode in an anode zone, the anode disposed relative to the cathode so as to be adapted to generate an electric field in an electric field area therebetween upon application of an electric potential between the cathode and the anode, a separation membrane disposed in the electric field area, a first restriction membrane disposed between a first electrode zone and the separation membrane so as to define a first interstitial volume therebetween, a second restriction membrane disposed between a second electrode zone and the separation membrane so as to define a second interstitial volume therebetween, an arrangement that provides solvent to the cathode zone, the anode zone and at least one of the first and second interstitial volumes, a system that provides a sample constituent in a selected one of the first interstitial and second interstitial volumes wherein upon application of the electric potential, a selected separation product is removed from the sample constituent through at least one membrane and provided to the other of the first and second interstitial volumes or the cathode or anode zones. The cathode zone and the anode zone are supplied with suitable solvent or buffer solutions by any suitable pumping means. A sample to be processed is supplied directly to the first or second interstitial volumes by any suitable pumping means. The first electrode is preferably the cathode and the second electrode is preferably the anode. Depending on the sample to be treated and the pH of the solvents or buffers used, the configuration can be reversed where the first electrode is the anode and the second electrode is the cathode.

In one suitable apparatus, the zones and the interstitial volumes are configured to allow flow of the respective fluid/buffer and sample solutions forming streams. In this form, large volumes can be processed quickly and efficiently. The solutions are typically moved or recirculated through the zones and volumes from respective reservoirs by suitable pumping means. For example, peristaltic pumps may be used as the pumping means for moving the sample, buffers or fluids.

In another suitable apparatus, a further arrangement removes heat generated in the electrophoresis apparatus. For example, samples and fluids are passed through heat exchangers to remove heat produced by the apparatus during electrophoresis. As another example, electrode buffer, other buffers, and sample solutions are cooled by any suitable arrangement to limit inactivation of compounds during the separation process and to maintain a desired temperature of the apparatus while in use.

In a suitable electrophoresis apparatus, the distance between the electrodes has an effect on the separation or movement of sample constituents through the membranes. The shorter the distance between the electrodes, the faster the electrophoretic movement of constituents. A distance of about 6 mm has been found to be suitable for a laboratory scale apparatus. For scale-up versions, the distance will depend on and volume of the chambers for samples, buffers and separated products. Preferred distances would be in the order of about 6 mm to about 10 cm. The distance will also relate to the voltage applied to the apparatus.

The effect of the electric field is based on the equation:

$$e = V/d$$

(e=electric field, V=voltage, d=distance)

Therefore, the smaller the distance between the electrodes the faster the separation. Preferably, the distance between the electrodes should decrease in order to increase electric field strength, thereby further improving transfer rates through the membranes.

Flow rate of sample/buffer/fluid has an influence on the separation of constituents. Rates of milliliters per minute up to liters per hour can be used depending on the configuration of the apparatus and the sample to be separated. For example, in one laboratory scale instrument, the preferred flow rate is about 20±5 mL/min. However, flow rates from about 0 mL/min to about 50,000 mL/min have also been used across various separation regimes. The maximum flow rate is even higher, depending on the pumping means and size of the apparatus. Other flow rates may also may be used. The selection of the flow rate is dependent on the product to be transferred, efficiency of transfer, pre- and post-positioning with other applications, and is readily ascertainable by one skilled in the art.

Selection or application of the voltage and/or current applied varies depending on the separation. Typically up to several thousand volts are used but choice and variation of voltage will depend on the configuration of the apparatus, buffers and the sample to be separated. In a laboratory scale instrument, the preferred voltage is about 250 V. However, depending on transfer, efficiency, scale-up and particular method, about 0 V to 5000 V are used. Higher voltages are also considered, depending on the apparatus and sample to be treated. Selection of a suitable voltage is readily ascertainable by practitioners skilled in the art.

Optionally, the electric potential may be periodically stopped and reversed to cause movement of a constituent having entered a membrane to move back into the volume or stream from which it came, while substantially not causing any constituents that have passed completely through a membrane to pass back through the membrane.

Reversal of the electric potential is an option but another alternative is a resting period. Resting (a period without an electric potential being applied) is an optional step that can replace or be included before or after an optional electrical potential reversal. This resting technique often can be practiced for specific separation applications as an alternative or adjunct to reversing the potential.

In another suitable apparatus and method, solution in at least one of the volumes or streams containing any separated compounds or molecules is collected and replaced with suitable solvent to ensure that electrophoresis can continue in an efficient manner. Suitable apparatus may also be adapted to accommodate large volume through-put as well as different separation configurations. While the various electrophoresis apparatus described above separate native or recombinant Factor VIII according to the present claims, other membrane-based electrophoresis apparatus known in the art are also suitable.

Referring to block 110, methods practiced according to the present claims provide one or more stabilizing agents to the sample and/or an interstitial volume. Stabilizing agents assist in maintaining the biological activity of the isolated FVIII. For example, buffering constituents, molarity altering components, proteins, amino acids, sugars or combinations thereof may be added as stabilizing agents. As other examples, sorbitol, salt, glycerol, sucrose, lactose, dextran/dextrose, glycine, gelatin, potassium acetate, azide, Synthamin 17 (Baxter Corporation) and protease inhibitors may also be used as stabilizing agents according to the present claims. Other suitable stabilizing agents for FVIII are known in the art and may also be used. In one embodiment, albumin, a mixture of amino acids, sucrose, or a mixture thereof are used as stabilizing agents. For example, in one embodiment, albumin is used at a concentration of at least about 2 mg/mL (2 g/L), a mixture of amino acids is used at a concentration of at least about 0.01 g/mL (10 g/L), and sucrose is used at a concentration of at least about 1% (10 g/L). In another embodiment, albumin is used at a concentration of about 10 mg/mL (10 g/L), the mixture of amino acids is used at a concentration of about 0.05 g/mL (50 g/L), and sucrose is used at a concentration of about 5% (50 g/L). It will be appreciated that the stabilizer can be added as part of the starting material or added to the sample before or during the electrophoresis separation. As an example, one or more stabilizing agents may be added to the sample and/or to the end product stream containing FVIII.

Block 120 selects a solvent having a pH such that FVIII has a desired charge state. Depending on the solvent, FVIII is maintained in either a positive, negative, or neutral charge state. For example, selecting a buffer having a pH greater than the pI value of FVIII maintains the FVIII in a negatively charged state. Selecting a buffer having a pH lower than the pI value of FVIII maintains the FVIII in a positively charged state. A buffer having a pH equal to the pI value of FVIII maintains the FVIII in a neutral charge state. In one embodiment, a buffer having a pH value between 6.5 to 7.0 results in FVIII having a net negative charge. In one embodiment, a combination of pH 6.5 (MES/Histidine), 1500 kDa separation membrane and 5 kDa restriction membranes was used. Obviously, other buffer selections may be used. The selection of buffer to maintain FVIII in a desired charge state is readily known to one skilled in the art.

Block 130 applies an electric potential between the first and second interstitial volumes wherein an end product containing FVIII is located on one side of the separation membrane while unwanted molecules are substantially located on the other side of the separation membrane. In one embodiment, the end product FVIII retains at least about 40% specific activity. Preferably, the specific activity is at least about 60%, and more preferably greater than about 75%. Specific activity can be calculated as μg FVIII obtained or mg total protein obtained.

Block 140 maintains the potential applied in block 130 until the desired amount of end product FVIII is located on one side of the separation membrane while unwanted molecules are located on the other side of the separation membrane. In one embodiment, commercial quantities of native FVIII or rFVIII are obtained having at least about 28% recovery and at least about 40% activity. However, other recovery amounts and activities are possible using the present methods described in the claims.

For example, in one embodiment, the sample containing FVIII is placed in a first interstitial volume of an electrophoresis apparatus comprising a separation membrane having a defined pore size with a molecular mass cut off greater than the molecular mass of FVIII disposed in the electric field area; a first restriction membrane disposed between a first electrode zone and the separation membrane so as to define a first interstitial volume therebetween; a second restriction membrane disposed between a second electrode zone and the separation membrane so as to define a second interstitial volume therebetween. One or more stabilizing agents is provided to the sample and/or the second interstitial volume. Selecting a solvent at a defined pH for the first interstitial volume results in the FVIII having a desired charge state. Applying an electric potential between the first and second interstitial volumes causes movement of FVIII in the first interstitial volume through the separation membrane into the second interstitial volume and forms an end product containing FVIII while unwanted molecules are substantially prevented from entering the second interstitial volume. The potential is applied until the desired amount of FVIII is moved to the second interstitial volume.

In another embodiment, a sample containing FVIII is placed in a first interstitial volume of an electrophoresis apparatus comprising a separation membrane having a defined pore size with a molecular mass cut off less than the molecular mass of FVIII disposed in an electric field area; a first restriction membrane disposed between a first electrode zone and the separation membrane so as to define a first interstitial volume therebetween; a second restriction membrane disposed between a second electrode zone and the separation membrane so as to define a second interstitial volume therebetween. One or more stabilizing agents is provided to the sample and/or the second interstitial volume. Selecting a solvent at a defined pH for the first interstitial volume results in the FVIII having a desired charge state. Applying an electric potential between the first and second interstitial volumes causes movement of components in the sample other than FVIII in the first interstitial volume through the separation membrane into the second interstitial volume while FVIII is substantially prevented from entering the second interstitial volume and is retained in the first interstitial volume as an end product. The applied potential is maintained until the desired amount of components in the sample are removed from the first interstitial volume and the end product FVIII is retained in the first interstitial volume.

In another embodiment, a sample is placed in the first interstitial volume, buffer or solvent is provided to the electrode zones and the second interstitial volume, an electric potential is applied to the electric field area causing at least one constituent in the sample to move to buffer/solvent in the cathode zone or buffer/solvent in the second interstitial volume. However, practitioners in the art will appreciate that the order of interstitial volumes can be reversed where a sample is placed in the second interstitial volume, buffer or solvent is provided to the electrode zones and the first interstitial volume, an electric potential is applied to the electric field area causing at least one constituent in the sample to move to buffer in the anode zone or buffer in the first interstitial volume. The claims also contemplate placing the sample in one (or both) of the electrophoresis zones and movement into one or more of the interstitial volumes is achieved during the application of the voltage potential.

FVIII may also be obtained substantially free from toxin, pathogen or infectious agent contamination in a sample. For example, some toxins, pathogens or infectious agents that may be removed include endotoxin, prion, viral, bacterial, fungal, yeast or protozoan. However, other toxin, pathogens or infectious agents may also be removed by a method practiced according to the present claims.

In one embodiment, the sample containing FVIII (and toxin, pathogen, or infectious agent contaminants) is placed in a first interstitial volume of an apparatus comprising a separation membrane having a defined pore size with a molecular mass cut off greater than the molecular mass of FVIII disposed in an electric field area; a first restriction membrane disposed between a first electrode zone and the separation membrane so as to define a first interstitial volume therebetween; a second restriction membrane disposed between a second electrode zone and the separation membrane so as to define a second interstitial volume therebetween. One or more stabilizing agents are provided to the sample and/or the second interstitial volume. Selecting a solvent with a defined pH for the first interstitial volume results in FVIII having a desired charge state. Applying an electric potential between the first and second interstitial volumes causes movement of FVIII in the first interstitial volume through the separation membrane into the second interstitial volume forming an end product while unwanted molecules and toxin, pathogen or infectious agent contaminants are substantially prevented from entering the second interstitial volume. The applied potential is maintained until the desired amount of FVIII is moved to the second interstitial volume and relatively free from toxin, pathogen or infectious agent contamination.

In another embodiment that removes toxins, pathogens or infectious agents, a sample of FVIII as an end product from block 140 is obtained. This sample may contain toxins, pathogens or infectious agents that were not removed in the process described in FIG. 1. The sample obtained from block 140 is placed in a first interstitial volume of an apparatus comprising a separation membrane having a defined pore size having a molecular mass cut off greater than that of FVIII disposed in an electric field area; a first restriction membrane disposed between a first electrode zone and the separation membrane so as to define a first interstitial volume therebetween; a second restriction membrane disposed between a second electrode zone and the separation membrane so as to define a second interstitial volume therebetween. Selecting a solvent for the first interstitial volume having a defined pH results in FVIII having a desired charge state. Applying an electric potential between the first and second interstitial volumes causes movement of FVIII in the first interstitial volume through the separation membrane into the second interstitial volume while the toxin, pathogen or infectious agent contaminants are substantially prevented from entering the second interstitial volume. The applied potential is maintained until the desired amount of FVIII is moved to the second interstitial volume and relatively free from toxin, pathogen or infectious agent contamination.

In still another embodiment that removes toxins, pathogens or infectious agents, a sample of FVIII as an end product from block 140 is obtained and placed in a first interstitial volume of an apparatus comprising a separation membrane having a defined pore size having a molecular mass cut off greater than toxin, pathogen or infectious agent disposed in an electric field area; a first restriction membrane disposed between a first electrode zone and the separation membrane so as to define a first interstitial volume therebetween; a second restriction membrane disposed between a second electrode zone and the separation membrane so as to define a second interstitial volume therebetween. Selecting a solvent for the first interstitial volume having a defined pH results in the toxin, pathogen, infectious agent contaminants having a desired charge state. Applying an electric potential between the first and second interstitial volumes causes movement of toxin, pathogen or infectious agent contaminants in the first interstitial volume through the separation membrane into the second interstitial volume while the FVIII is substantially prevented from entering the second interstitial volume. The applied potential is maintained until the desired amount of FVIII in the first interstitial volume is relatively free from toxin, pathogen or infectious agent contamination.

To assist in understanding the present application, the following examples are included and describe the results of a series of experiments. The following examples relating to this application should not be construed to specifically limit the application or such variations of the application, now known or later developed, which fall within the scope of the application as described and claimed herein.

Definitions

The term "FVIII activity" refers to the FVIII activity of the sample measured in IU/mL normal plasma.

The term "FVIII specific activity" refers to the FVIII activity of the sample measured in IU/mL as a function of the amount of FVIII antigen or total protein in IU/mL or mg/mL, respectively.

The term "stream 1 (S1)" refers to denote the first interstitial volume where sample is supplied in a stream to the electrophoresis apparatus.

The term "stream 2 (S2)" is used in this specification to denote the second interstitial volume where material is moved from the first interstitial volume through the separation membrane to a stream of the electrophoresis apparatus.

The term "forward polarity" is used when the first electrode is the cathode and the second electrode is the anode in the electrophoresis apparatus and current is applied accordingly.

The term "reverse polarity" is used when polarity of the electrodes is reversed such that the first electrode becomes the anode and the second electrode becomes the cathode.

Analytical Methods

Polyacrylamide Gel Electrophoresis (PAGE)

PAGE was used to measure the movement of components during an electrophoresis run. Standard PAGE methods were employed as set out below.

Reagents: 10× SDS Glycine running buffer (Gradipore Limited, Australia), dilute using Milli-Q water to 1× for use; 1× SDS Glycine running buffer (29 g Trizma base, 144 g Glycine, 10 g SDS, make up in RO water to 1.0 L); 10× TBE II running buffer (Gradipore), dilute using Milli-Q water to 1× for use; 1× TBE II running buffer (10.8 g Trizma base, 5.5 g Boric acid, 0.75 g EDTA, make up in RO water to 1.0 L); 2× SDS sample buffer (4.0 mL, 10% (w/v) SDS electrophoresis grade, 2.0 mL Glycerol, 1.0 mL 0.1% (w/v) Bromophenol blue, 2.5 mL 0.5M Tris-HCl, pH 6.8, make up in RO water up to 10 mL); 2× Native sample buffer (10% (v/v) 10× TBE II, 20% (v/v)PEG 200, 0.1g/L Xylene cyanole, 0.1 g/L Bromophenol blue, make up in RO water to 100%); Coomassie blue stain (Gradipure™, Gradipore Limited). Note: contains methanol 6% Acetic Acid solution for de-stain.

Molecular weight markers (Recommended to store at −20° C.): SDS PAGE (e.g. Sigma wide range); native PAGE (e.g. Gradipore native marker); Western Blotting (e.g. color/rainbow markers).

SDS PAGE with Non-reduced Samples

To prepare the samples for running, 2× SDS sample buffer was added to sample at a 1:1 ratio (usually 50 μL/50 μL) in the microtiter plate wells or 1.5 mL tubes. The samples were incubated for 5 minutes at approximately 100° C. Gel cassettes were clipped onto the gel support with wells facing in, and placed in the tank. If only running one gel on a support, a blank cassette or plastic plate was clipped onto the other side of the support Sufficient 1× SDS glycine running buffer was poured into the inner tank of the gel support to cover the sample wells. The outer tank was filled to a level approximately midway up the gel cassette. Using a transfer pipette, the sample wells were rinsed with the running buffer to remove air bubbles and to displace any storage buffer and residual polyacrylamide.

Wells were loaded with a minimum of 5 μL of marker and the prepared samples (maximum of 40 μL). After placing the lid on the tank and connecting leads to the power supply the gel was run at 150V for 90 minutes. The gels were removed from the tank as soon as possible after the completion of running, before staining or using for another procedure (e.g. Western blot).

Staining and De-Staining of Gels

The gel cassette was opened to remove the gel which was placed into a container or sealable plastic bag. The gel was thoroughly rinsed with tap water, and drained from the container. Coomassie blue stain (approximately 100 mL Gradipure™, Gradipore Limited, Australia)) was added and the container or bag sealed. Major bands were visible in 10 minutes but for maximum intensity, stain overnight. To de-stain the gel, the stain was drained off from the container.

The container and gel were rinsed with tap water to remove residual stain. 6% acetic acid (approximately 100 mL) was poured into the container and sealed. The de-stain was left for as long as it takes to achieve the desired level of de-staining (usually 12 hours). Once at the desired level, the acetic acid was drained and the gel rinsed with tap water.

A time course of the starting material and final product were run on 4–20% SDS-PAGE igels™ (Gradipore Limited, Australia). The gels were then stained using Gradipure™ Coomassie blue stain (Gradipore Limited, Austral Isoelectric Focusing (IEF)

IEF was used to determine isoelectric points of components to assist in devising electrophoresis separation conditions. Standard IEF methods were employed as set out below.

Reagents: Novex® IEF Gels were used for pI determination and confirmation of isoforms of purified products. Novex® IEF Gels are 5% polyacrylamide, non-denaturing, and do not contain urea. The pH 3–10 gels have a pI performance range of 3.5–8.5.

Recommended Buffers: pH 3–10 IEF Gels (Novex® IEF Sample Buffer, pH 3–10 (2×) 25 mL, Cat. No. LC5311; Novex® IEF Cathode Buffer, pH 3–10 (10×) 125 mL, Cat. No. LC5310; Novex® IEF Anode Buffer, (50×) 100 mL, Cat. No. LC5300); IEF Cathode Buffers (1× working solutions) were degassed for 10 minutes under vacuum or purged 1 minute with inert gas just before using.

Fixing Solution: 17.3 g Sulphosalicylic acid, 57.3 g TCA, D.I. water fill to 500 mL, IEF, pH 3–7 Catalog # LC5371 (2×), 2.0 mL 10× Cathode Buffer (3–7), 3.0 mL Glyce water to 10.0 mL, Cathode Buffer, Cat. # LC5370 (10×), 5.8 g Lysine (free base), Distilled Water to 100 mL, Anode Buffer, Cat. # LC5300 (50×), 4.7 g Phosphoric Acid (85%), Distilled Water to 100 mL. 1× anode buffer should be ~pH 2.4. 10× cathode buffer should be 10.1.

Protocol

Sample was prepared by adding one part sample to one part Novex® IEF Sample Buffer (2×) and mixed well.

Novex® IEF Cathode Buffer (10×) was diluted 1:9 with deionized water before use and the IEF Cathode Buffer (1× working solutions) degassed for 10 minutes under vacuum, or purged 1 minute with nitrogen or helium gas just before using. This reduces the possibility of bubbles from dissolved carbon dioxide forming during the gel run. The upper buffer chamber was filled with the appropriate amount of Cathode Buffer.

Novex® IEF Anode Buffer (50×) was diluted 1:49 with deionized water before use and the appropriate amount of Anode Buffer poured into the lower buffer chamber.

An appropriate volume of sample was loaded into the wells which have been filled with Novex® IEF Cathode Buffer.

The gel was run according to the following running conditions: 100V constant—1 hour, 200V constant—1 hour, 500V constant—30 minutes, The approximated current started at 5 mA/gel and ended at 6 mA/gel. The run time was approximately 2.5 hours.

After the run, the gel was removed from the cassette and fixed in the fixing solution (see above for recipe) for 30 minutes. This step is important to fix the proteins and to remove the ampholytes. Otherwise, a high background may result.

The gel was placed in stain (0.1% Coomassie R-250) and shaken for 5 minutes. The gel was destained with a 1× solution of destain or Novex® Gel-Clear™ destain until the desired clarity was achieved. All fixing, staining and destaining was performed with gentle shaking.

Purified FVIII was run on an IEF gel at two different dilutions. The IEF gel was blotted onto nitrocellulose, which was probed with a mouse anti-human FVIII primary antibody. A secondary antibody which was HRP conjugated was used to probe the primary antibody and developed using 4CN. The isoelectric point of Porcine Parvo virus (PPV) was also determined by IEF as set out below.

Synthamin 17

Synthamin 17 is an intravenous infusion solution of 14 L-amino acids at 0.1 g/mL available from Baxter. This solution was used as a source of synthetic amino acids. Each 1000 mL of Synthamin 17 (Amino Acid) (10%) Intravenous Infusions without electrolytes contains

| L-Amino Acids | 100 g |
| Total Nitrogen | 5.5 g |
| Approximate pH | 6.0 |
| Protein Equivalents | 103 g |
| Essential Amino Acids | |
| | |
| L-Leucine | 7.30 g |
| L-Phenylalanine | 5.60 g |
| L-Methionine | 4.00 g |
| L-Lysine (added as the Hydrochloride salt) | 5.80 g |
| L-Isoleucine | 6.00 g |
| L-Valine | 5.80 g |
| L-Histidine | 4.80 g |
| L-Threonine | 4.20 g |
| L-Tryptophan | 1.80 g |
| Non-Essential Amino Acids | |
| | |
| L-Alanine | 20.7 g |
| Aminoacetic Acid (Glycine) | 10.3 g |
| L-Arginine | 11.5 g |
| L-Proline | 6.80 g |
| L-Tyrosine | 400 mg |
| L-Serine | 5.00 g |

Approximately 1.5 mmol/L Sodium Metabisulphine BP is added as stabilizer

Experimental Protocols and Results

Characterizing FVIII from a Purified Source

The following experiments established a pH suitable for FVIII movement in the electrophoresis system. Approximately 100 IU/mL of FVIII in the experimental buffer was used as a starting material. A pH range of 5.0–7.5 and large pore size separation membranes (500–1000 kDa) were investigated allowing FVIII movement on the basis of charge rather than size. Maintaining stability of FVIII limited the experiments to this pH range. Analysis of FVIII movement and activity was conducted using chromogenic assays and FVIII specific activity is expressed as the amount of FVIII activity (IU) per μg of FVIII. Assumptions were made on the movement of the other proteins in the product from their quoted/theoretical pI and size (kDa).

Separation with buffers at pH 7.1 and pH 7.3 (Hepes/Imidizole) used a 5-800-5 kDa membrane configuration (first restriction membrane-separation membrane-second restriction membrane). Separation with buffers at pH 6.7 (Hepes/Imidizole) used a 5-1000-5 kDa membrane configuration. Separation with buffers at pH 6.5 (MES/Histidine) and pH 5.0 (GABA/Acetic Acid) used a 5-1500-5 kDa membrane configuration.

Results from FVIII Concentrate Using Large Pore Size Membranes in a pH Range

Figure 2:
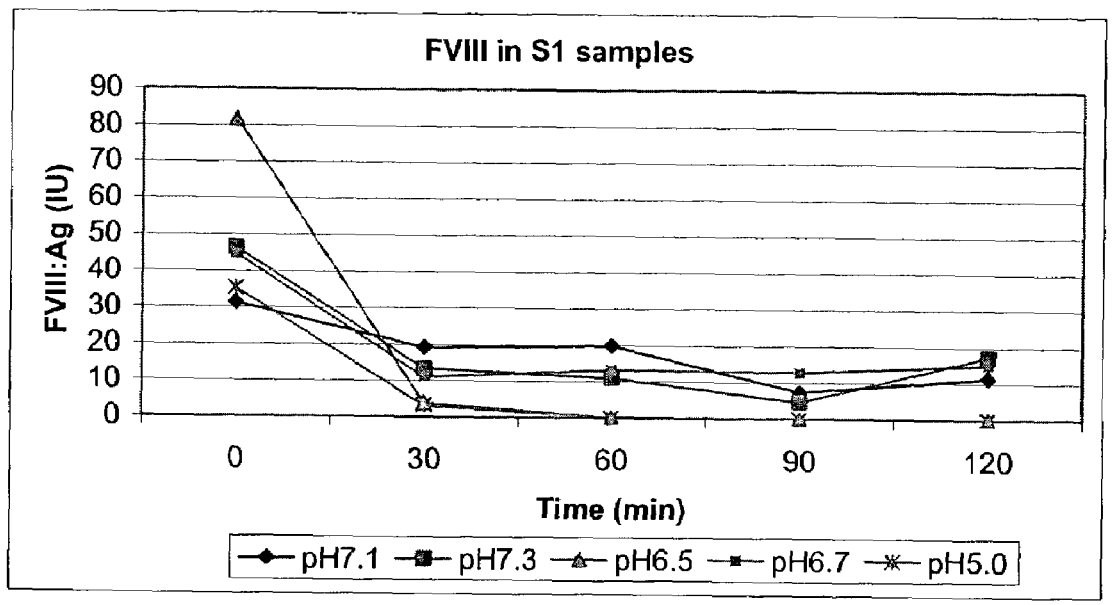
FIG. 2 illustrates the movement of FVIII antigen (FVIII: Ag) in S1 of the electrophoresis system at various pH values over time.

FIG. 2 illustrates the movement of FVIII antigen (FVIII:Ag) in S1 of the electrophoresis system at various pHs. These results indicate that the majority of the FVIII:Ag moved out of the S1 within the first 30 min at each pH tested under forward polarity, indicating that none of the pH values tested are equivalent to the pI value of FVIII: i.e., at all the pH values tested, FVIII remained in a charged state.

Figure 3:
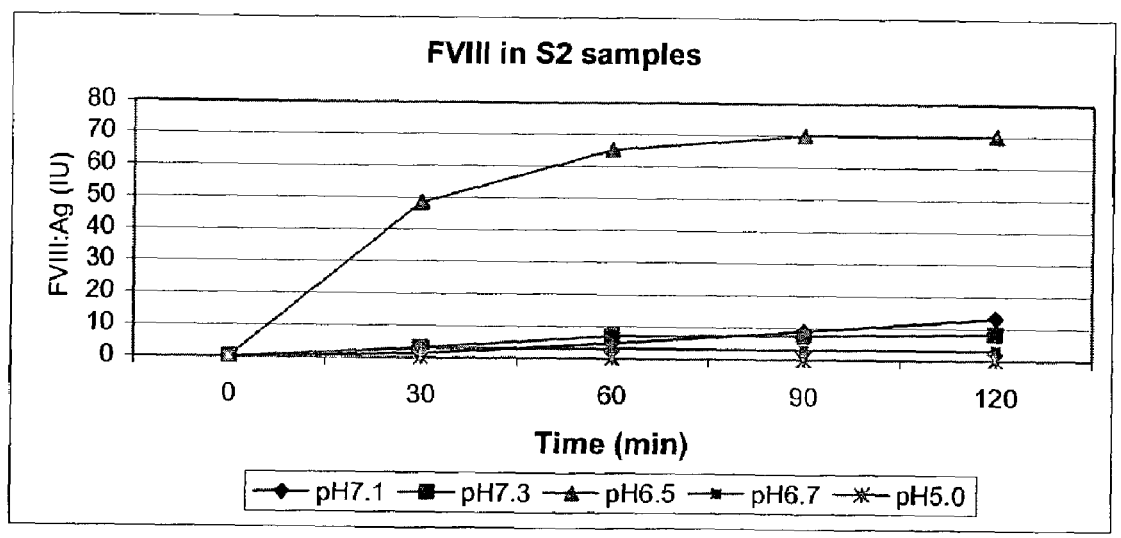
FIG. 3 illustrates the movement of FVIII:Ag in S2 of the electrophoresis system at various pH values over time.

FIG. 3 illustrates the movement of FVIII:Ag in S2 of the electrophoresis system at various pHs. These results indicate that FVIII:Ag is detected at low levels in S2 for pH 6.7, 7.3 and 7.5 and not at all for pH 5.0. At pH 6.5, FVIII:Ag was detected in S2 at significant levels.

Therefore, at >pH 6.5, FVIII is negatively (−ve) charged and moves out of the S1 and into S2 under forward polarity.

The absence of FVIII in S2 can be explained as either FVIII being clogged or bound to the separation membrane or that FVIII was highly charged and bound to the lower or second restriction membrane. At pH 5.0, FVIII moved from S1 but did not appear in S2, indicating that at this pH, FVIII was positively (+ve) charged migrating to the top or first restriction membrane under forward polarity.

While it can be important to retain FVIII:Ag in the system, without antigen present a level of activity could not be detected. Where the experimental conditions included a buffer at pH 6.5 (MES/Histidine), 5-1500-5 kDa membrane configuration, 30 min harvest with resting and reversal (2 min) for 2 hours, assays (at 30 minute intervals) demonstrated that a total of 90.3% FVIII antigen recovery at 2 hours (US=4.78%, S2=85.52%), thus indicating that functional activity was maintained throughout the separation. Specific activity of each S2 fraction is represented in Table 1.

TABLE 1

FVIII antigen recovery and specific activity as a % of $S1_0$ at pH 6.5

| $Sample_{(min)}$ | FVIII antigen as % of $S1_0$ | FVIII specific activity as % of $S1_0$ |
|---|---|---|
| $S1_0$ | 100.00 | 100.00 |
| $S2_0$ | 0.00 | 0.00 |
| $S2_{30}$ | 59.19 | 87.2 |
| $S2_{60}$ | 20.54 | 21.92 |
| $S2_{90}$ | 5.79 | 8.23 |
| $S2_{120}$ | 0.00 | 0.00 |

At pH 6.5, 59.19% of FVIII was transferred to the $S2_{30}$ harvest. The majority of the stabilizing albumin in the preparation also migrated to S2. FVIII in the $S2_{30}$ sample was highly stable (87.2%) probably as a result of the albumin which was also harvested at this time point. The remaining S2 fractions collected FVIII but with a considerably diminished activity level as a result of the majority of the stabilizing albumin collected in the first fraction ($S2_{30}$).

Calculation of FVIII Concentrate pI

The theoretical pI of human FVIII is 6.97, calculated from its amino acid sequence. Often these theoretical pI calculations do not correlate to the biological entity as demonstrated by the FVIII results above. If the pI of FVIII was in fact 6.97, there should not have been movement to S2 at pH 6.5 under forward polarity. The above results indicate that the pI of FVIII from the experimental preparation was between 5.0<6.5.

Figure 4:
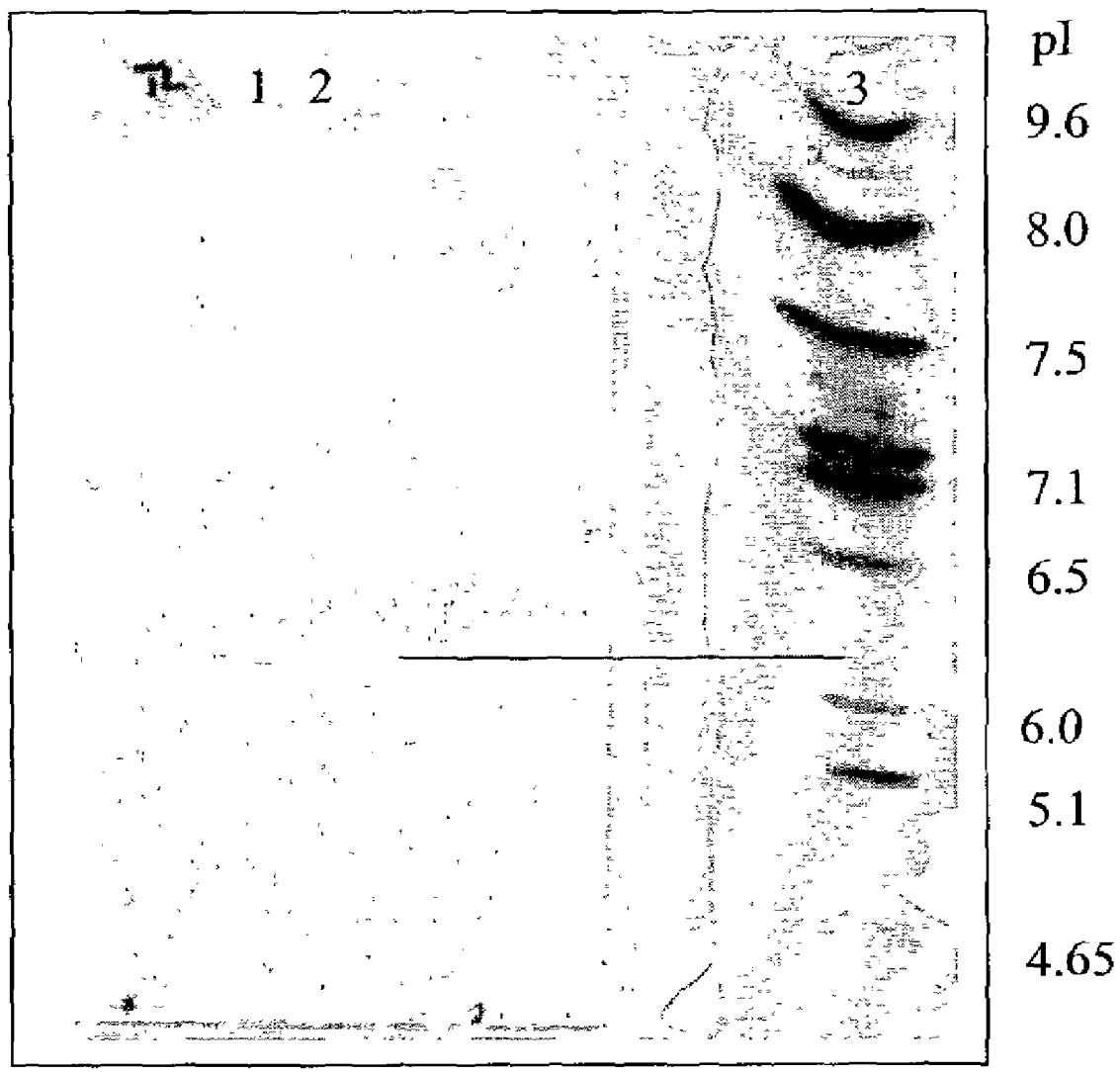
FIG. 4 shows an isoelectric focusing Western blot of FVIII from a highly purified product probed with mouse anti-human FVIII. The results indicate a true pI of 6.2 for FVIII from this source which demonstrates the movement results at various pH values.

To supplement the electrophoresis separation experiments, isoelectric focusing (IEF) was used to calculate the pI value of FVIII. FIG. 4 shows an isoelectric focusing Western blot of FVIII probed with mouse anti-human FVIII. The results indicate a pI of 6.2 for FVIII which supports the electrophoresis movement results at various pH values reported above.

Stabilizing Agents for FVIII Concentrate

These experiments highlight the instability of the FVIII molecule and the positive effect stabilizing agents have on the movement and activity of FVIII.

Proteins

The following experiments demonstrate that a constant albumin concentration can be delivered to the FVIII molecule during the course of separation using the present methods.

Experiment 1

Separation conditions: pH 6.5 (MES/Histidine) buffer, 5-1500-5 kDa cartridge configuration, 30 min harvest with resting and reversal for 2 hours. The replenishing S2 buffer after electrophoretic harvesting of FVIII contained human albumin at a final concentration of 10 mg/mL.

Figure 5:
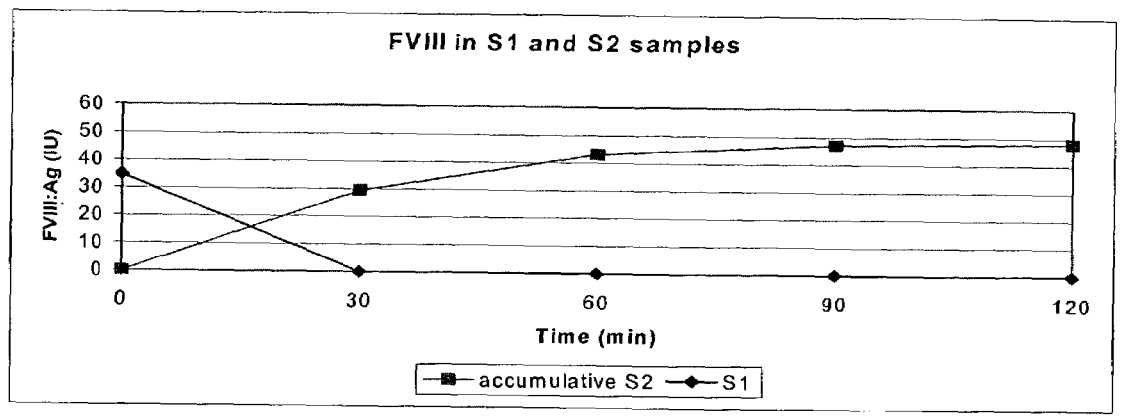
FIG. 5 illustrates the movement of FVIII:Ag in S1 and S2 of an electrophoresis apparatus using albumin as a stabilizing agent in the running buffer (final concentration of albumin at 10 mg/mL)

FIG. 5 shows the movement of FVIII:Ag in S1 and S2 of the apparatus using human albumin as a stabilizing agent in S2 replenishing buffer (final concentration 10 mg/mL).

TABLE 2

FVIII antigen recovery and specific activity as a percentage of $S1_0$ for the experiment using human albumin as a stabilizing agent in S2 replenishing buffer (final concentration 10 mg/mL).

| $Sample_{(min)}$ | FVIII antigen as % of $S1_0$ | FVIII specific activity as % of $S1_0$ |
|---|---|---|
| $S1_0$ | 100.00 | 100.00 |
| $S2_0$ | 0.00 | 0.00 |
| $S2_{30}$ | 84.48 | 76.19 |
| $S2_{60}$ | 39.37 | 87.46 |
| $S2_{90}$ | 11.78 | 87.70 |
| $S2_{120}$ | 2.30 | 139.68 |

The addition of human albumin into S2 buffer had a positive effect on retaining FVIII activity in the electrophoresis apparatus. The stabilizing effect of the additional albumin was not evident on FVIII specific activity in the first S2 harvest ($S2_{30}$) as it contained albumin from the starting material transferred to the S2. The remaining S2 harvests had an increased specific activity due to the addition of the stabilizing albumin in contrast to the parallel experiment not containing stabilizing albumin (results shown in Table 2).

Therefore, the addition of albumin to S2 running buffer was evidence that a stabilizing agent can be added to the system during the purification / isolation procedure, and can have a positive effect on retaining the specific activity of FVIII.

Amino Acids

The following experiments demonstrate that amino acids may be effectively used as a stabilizing agent. The protocol involved a cartridge configuration with larger restriction membranes (35-1500-35 kDa). This configuration enables reasonably constant circulation of amino acids contained in the running buffer through S1, S2 and the buffer stream.

Experiment 2

Separation conditions: pH 6.5 (MES/Histidine) buffer and Synthamin 17 (1:1 ratio, Synthamin 17 final concentration was 0.05 g/mL), 35-1500-35 kDa cartridge configuration, 30 min harvest with resting and reversal for 2 hours was used. The final pH of the buffer was 6.2 due to the influence of the Synthamin 17.

Figure 6:
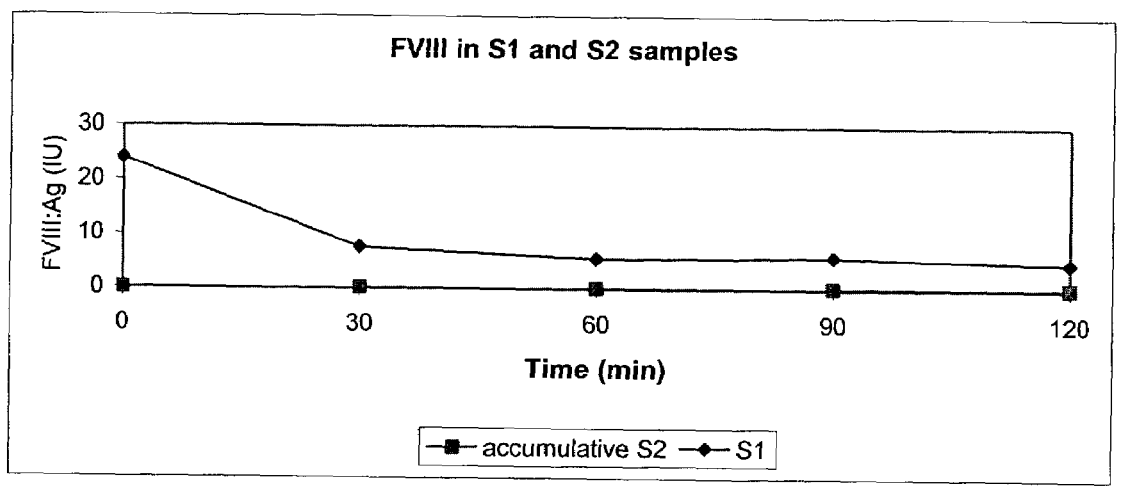
FIG. 6 illustrates the movement of FVIII:Ag in S1 and S2 of an electrophoresis apparatus using Synthamin 17 as a stabilizing agent in the running buffer (final concentration of Synthamin 17 at 0.05 g/mL)

FIG. 6 shows the movement of FVIII:Ag in S1 and S2 of an electrophoresis apparatus using Synthamin 17 as a stabilizing agent in the running buffer (final concentration 0.05 g/mL). Not only did the Synthamin 17 influence the final pH of the buffer it also affected the current, which was a limiting factor at 500 mA. These conditions resulted in low voltage, approximately 40V for the duration of the experiment (Table 3). At 120 min a total of 20.16% of FVIII was retained in S1 with 83.39% of the initial activity. The retention of FVIII activity for the 30 min and 60 min harvests was evidence that the Synthamin 17 has a positive effect on retaining FVIII activity. Under the low voltage conditions it was expected that albumin in the preparation would move very slowly into S2 and hence may be present in S1 as a stabilizer for FVIII.

TABLE 3

FVIII antigen recovery and specific activity as a percent of $S1_0$ for the experiment using Synthamin 17 as a stabilizing agent in the running buffer (final concentration 0.05 g/mL).

| Sample$_{(min)}$ | FVIII antigen as % of $S1_0$ | FVIII specific activity as % of $S1_0$ |
|---|---|---|
| $S1_0$ | 100.00 | 100.00 |
| $S1_{30}$ | 31.70 | 133.6 |
| $S1_{60}$ | 23.54 | 133.9 |
| $S1_{90}$ | 24.82 | 80.64 |
| $S1_{120}$ | 20.16 | 83.39 |
| $S2_0$ | 0.00 | 0.00 |
| $S2_{30}$ | 4.45 | 6.62 |
| $S2_{60}$ | 2.7 | 0.00 |
| $S2_{90}$ | 1.66 | 0.00 |
| $S2_{120}$ | 1.45 | 0.00 |

Experiment 3

Separation conditions: pH 6.5 (MES/Histidine) buffer and Synthamin 17 (3:1 ratio, Synthamin 17 final concentration was 0.025 g/mL), 35-1500-35 kDa cartridge configuration, 30 min harvest with resting and reversal for 2 hours. The final pH of the buffer was 6.42 due to the influence of the Synthamin 17.

Figure 7:
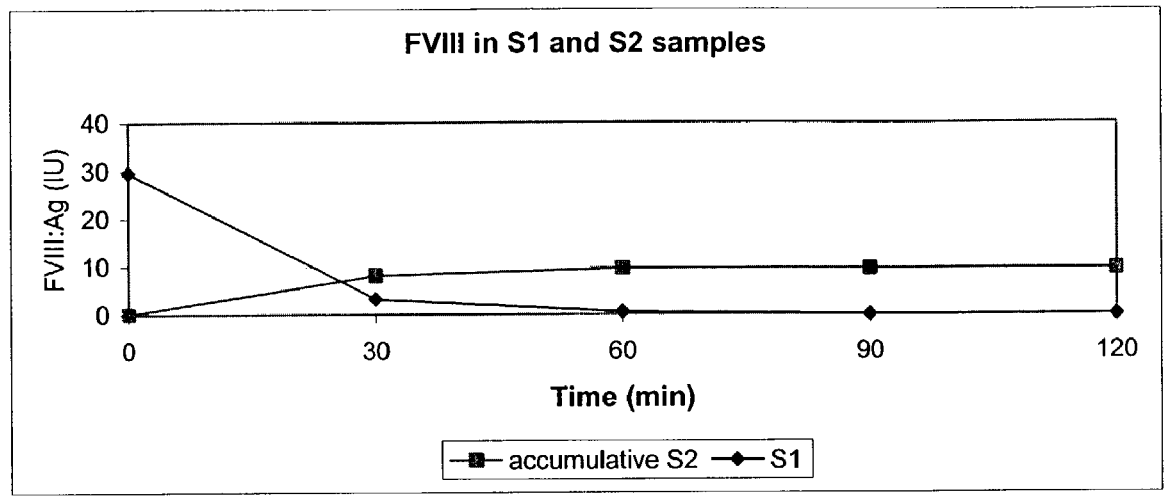
FIG. 7 illustrates the movement of FVIII:Ag in the S1 and S2 of the electrophoresis apparatus using Synthamin 17 as a stabilizing agent in the running buffer (final concentration of Synthamin 17 at 0.025 g/mL)

FIG. 7 illustrates the movement of FVIII:Ag in the S1 and S2 of the electrophoresis apparatus using Synthamin 17 as a stabilizing agent in the running buffer (final concentration 0.025 g/mL).

TABLE 4

FVIII antigen recovery and specific activity as a percent of $S1_0$ for the experiment using Synthamin 17 as a stabilizing agent in the running buffer (final concentration 0.025 g/mL).

| Sample$_{(min)}$ | FVIII antigen as % of $S1_0$ | FVIII specific activity as % of $S1_0$ |
|---|---|---|
| $S1_0$ | 100.00 | 100.00 |
| $S1_{30}$ | 10.89 | 125.93 |
| $S1_{60}$ | 1.86 | 456.05 |
| $S1_{90}$ | 0.00 | 0.00 |
| $S1_{120}$ | 0.00 | 0.00 |
| $S2_0$ | 0.00 | 0.00 |
| $S2_{30}$ | 27.53 | 38.96 |
| $S2_{60}$ | 5.07 | 19.01 |
| $S2_{90}$ | 0 | 0.00 |
| $S2_{120}$ | 0 | 0.00 |

Using a lower concentration of Synthamin 17 (0.025 g/mL) also had a dramatic affect on the current, which was the limiting factor at 500 mA. These conditions resulted in low voltage, approximately 70V for the duration of the experiment. The higher pH in this experiment in comparison with experiment 1 (described above) resulted in more charge on FVIII allowing more movement into S2 (10.26% and 32.6% respectively). The influence of Synthamin 17 at this concentration on FVIII activity was a positive one, even though the $S1_{60}$ result was irregular.

Sugars

As seen in the experiments below, sugars also can be an alternative source of stabilizing agent for FVIII.

Characterization of FVIII from Plasma

Neat plasma was used as the source of FVIII. It was expected that the FVIII molecule would be bound to vWf in the plasma starting material forming a large complex. It was for this reason that it was expected that the vWf-FVIII complex would remain in S1 while contaminating plasma protein transferred to S2. A pH range of 5.5–7.3 was investigated in combination with a 1000 kDa separation membrane. Maintaining the stability of FVIII limited the experiments to this pH range. Analysis of FVIII movement and activity was conducted using chromogenic assays and its specific activity is expressed as the amount of FVIII activity (IU) per µg of FVIII in the sample of interest.

Results from FVIII Neat Plasma in a pH Range

Figure 8:
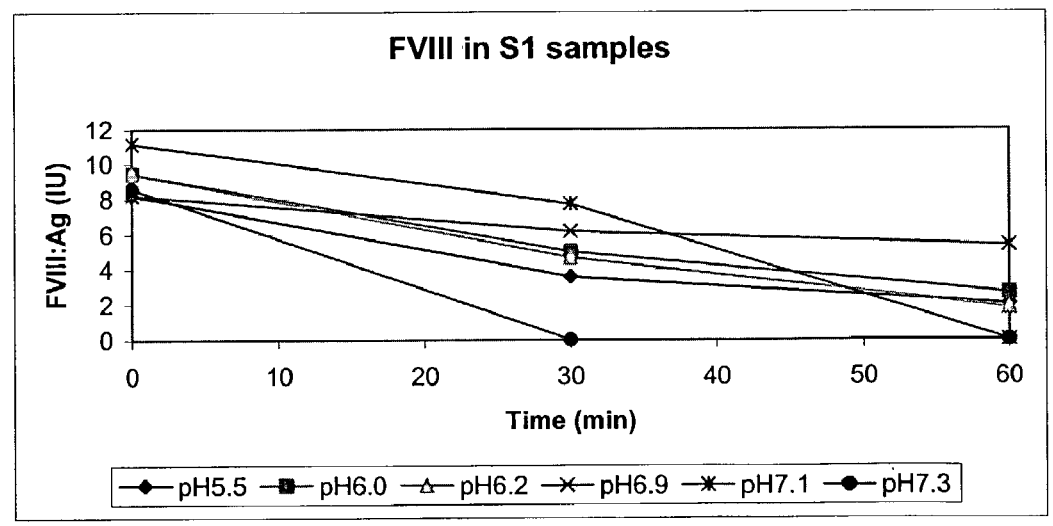
FIG. 8 illustrates the movement of FVIII:Ag in S1 of an electrophoresis apparatus at various pH values using neat plasma as starting material.

FIG. 8 shows the movement of FVIII:Ag in S1 of the electrophoresis apparatus at various pH values using neat plasma as the starting material. For all pH values analyzed, no FVIII:Ag transferred to S2 was noted.

TABLE 5

FVIII: Ag profile in the S1 as a % of $S1_0$ for the neat plasma experiments in the Gradiflow at various pH values.

| Sample | pH 5.5 | pH 6.0 | pH 6.2 | pH 6.9 | pH 7.1 | pH 7.3 |
|---|---|---|---|---|---|---|
| $S1_0$ | 100.00 | 100.00 | 100.00 | 100.00 | 100.00 | 100.00 |
| $S1_{30}$ | 43.80 | 52.99 | 49.47 | 75.07 | 69.20 | 0.00 |
| $S1_{60}$ | 24.76 | 28.07 | 19.19 | 65.15 | 0.00 | 0.00 |

The above results in Table 5 illustrate the movement of FVIII from neat human plasma in the system and pH 6.9 being a suitable running condition at this stage, retaining 65.15% of the starting FVIII at 60 min. A loss of 25% in the first 30 minutes and a further 10% in the second 30 minutes was observed under these conditions. FVIII may be binding non-specifically to membranes. This binding may be reduced by incorporating a PBS wash, resting, addition of Tween 20 in the buffer and/or diluting the starting material.

TABLE 6

FVIII antigen recovery and specific activity as a % of $S1_0$ at pH 6.9 using FVIII from plasma as a starting material.

| Sample$_{(min)}$ | FVIII antigen as % of $S1_0$ | FVIII specific activity as % of $S1_0$ |
|---|---|---|
| $S1_0$ | 100.00 | 100.00 |
| $S1_{30}$ | 75.07 | 65.95 |
| $S1_{60}$ | 65.15 | 78.82 |

Table 6 illustrates that the specific activity recovery of FVIII from neat plasma at pH 6.9. Since FVIII would be bound to vWf in the plasma, the loss of activity may be due to its activation and consequently deactivation in the coagulation cascade during the time the plasma is circulating in the separation apparatus.

The total protein of S1 samples containing the FVIII was not calculated but SDS-PAGE showed that a large proportion of plasma protein remained in the S1 under these conditions.

Characterizing FVIII with Porcine Parvo Virus (PPV)

PPV was used to demonstrate the removal of viral contaminants from FVIII using the present methods.

Calculating PPV pI

In order to utilize virus pI values in charged-based clearance or removal it was necessary to establish the pI value of PPV. Isoelectric focusing (IEF) was initially used to calculate the pI of PPV.

Figure 9:
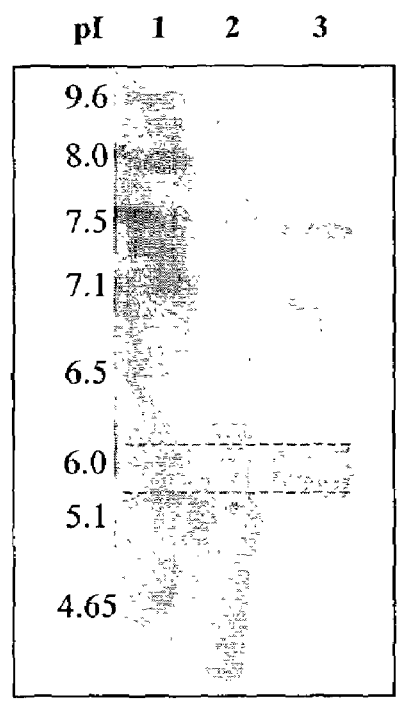
FIG. 9 is an isoelectric focussing (IEF) blot of porcine parvo virus (PPV) where Lane 1 is a pI marker stained with ponceaus S stain, lane 2 is PPV preparation stained with ponceaus S stain, lane 3 is PPV preparation probed with mouse anti-porcine parvo virus.

FIG. 9 is an IEF blot of PPV where Lane 1 is a pI marker stained with ponceaus S stain, lane 2 is PPV preparation stained with ponceaus S stain, lane 3 is PPV preparation probed with mouse anti-porcine parvo virus. These results indicate a pI range of 5.1 to 6.0 for PPV. The three other bands in lane 3 are not reactions with the mouse anti-parvo virus antibody and therefore do not represent any pI indications for PPV.

Figure 10:
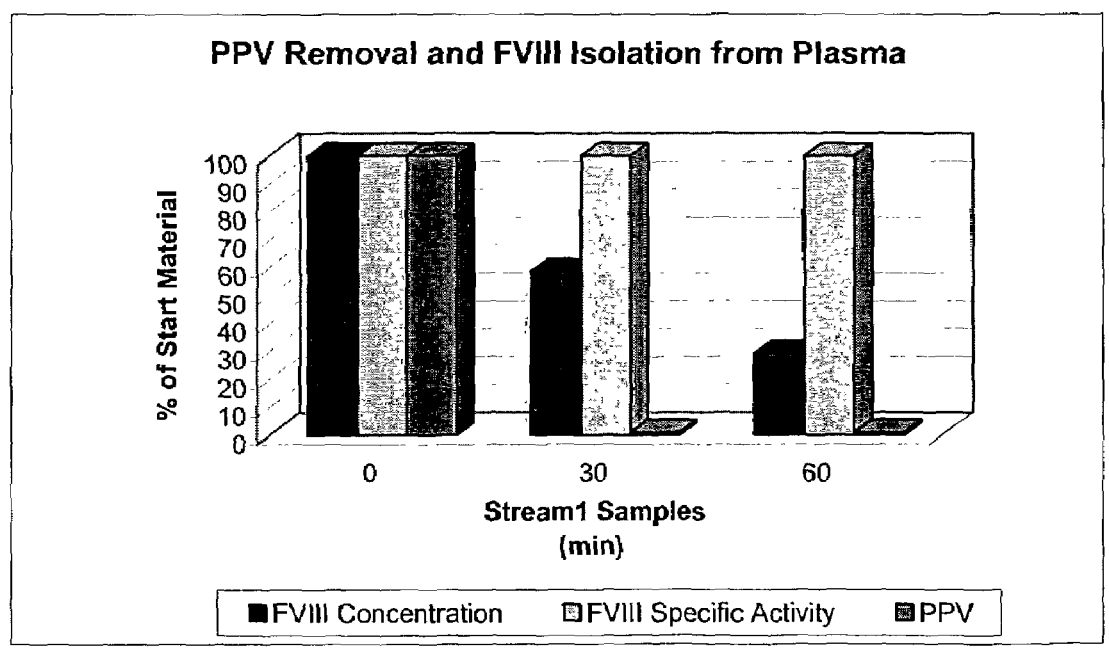
FIG. 10 is a graph showing the separation of FVIII from PPV contamination over time during an electrophoresis run.

FIG. 10 shows the results of the removal of PPV from FVIII by a method according to the present claims. When using plasma as a source of FVIII the viral load was decreased by retaining FVIII in S1 and allowing the virus to move through the membrane into S2. During the separation, FVIII-specific activity was retained as a result of the factor being bound to vWf while PPV was reduced to less than 1% of the starting load.

Recombinant Factor VIII (rFVIII) Purification

The experiments outlined above demonstrate that membrane-based electrophoresis methods may be utilized to separate FVIII from both a concentrated freeze-dried source and normal pooled plasma. The following experiments illustrate the purification of FVIII from a recombinant source. rFVIII protein was purified from contaminating cell culture media proteins.

rFVIII was spiked into S1 of the electrophoresis apparatus to produce approximately 10 IU of rFVIII activity per milliliter of solution. Initial experiments used a large pore size (LPS) membrane >1500K and pH 6.5 MES/Bis-Tris buffer. These conditions move rFVIII across a membrane while still retaining rFVIII in active form.

Figure 11:
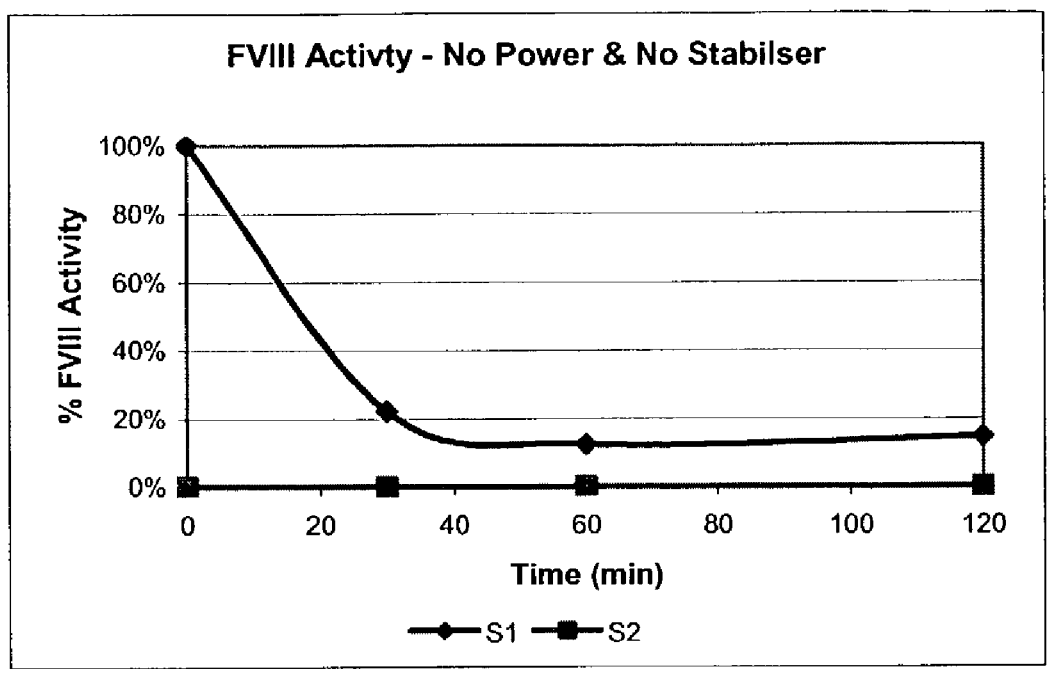
FIG. 11 is a graph showing the rFVIII activity found in S1 and S2 of the membrane-based electrophoresis apparatus when rFVIII wa power was applied across the separation unit.

When rFVIII was placed into standard MES/Bis-Tris buffer with no stabilizing agents, and circulated in the electrophoresis apparatus, the level of rFVIII activity quickly fell. Even though no power was applied across the separation unit only 15% of rFVIII activity remained after one hour of circulation (FIG. 11). This lower activity may have been due to the buffer not being optimal for the rFVIII molecule to retain function.

When power was applied across the separation unit, the level of activity in S1 also dropped dramatically and transient rFVIII activity was found in S2. All rFVIII activity could not be detected from both S1 and S2 within two hours when an electrical potential was applied. Due to the transient level of activity found in S2, it was decided that harvesting was useful to capture the active rFVIII after it was transferred.

FIG. 11 shows that the buffer and/or the conditions in the machine are detrimental to the rFVIII molecule. Almost all of the rFVIII activity was lost by the end of the two-hour separation. In order to test if it was the buffer or the apparatus that was causing the loss of functional activity, two different stabilizers, human serum albumin (HSA) and sucrose, were utilized. HSA often has been used to stabilize FVIII. Due to the problems of possible pathogen contamination from such proteins, artificial stabilizers are the preferred form. Sucrose has been used as an alternative stabilizing agent.

Figure 12:
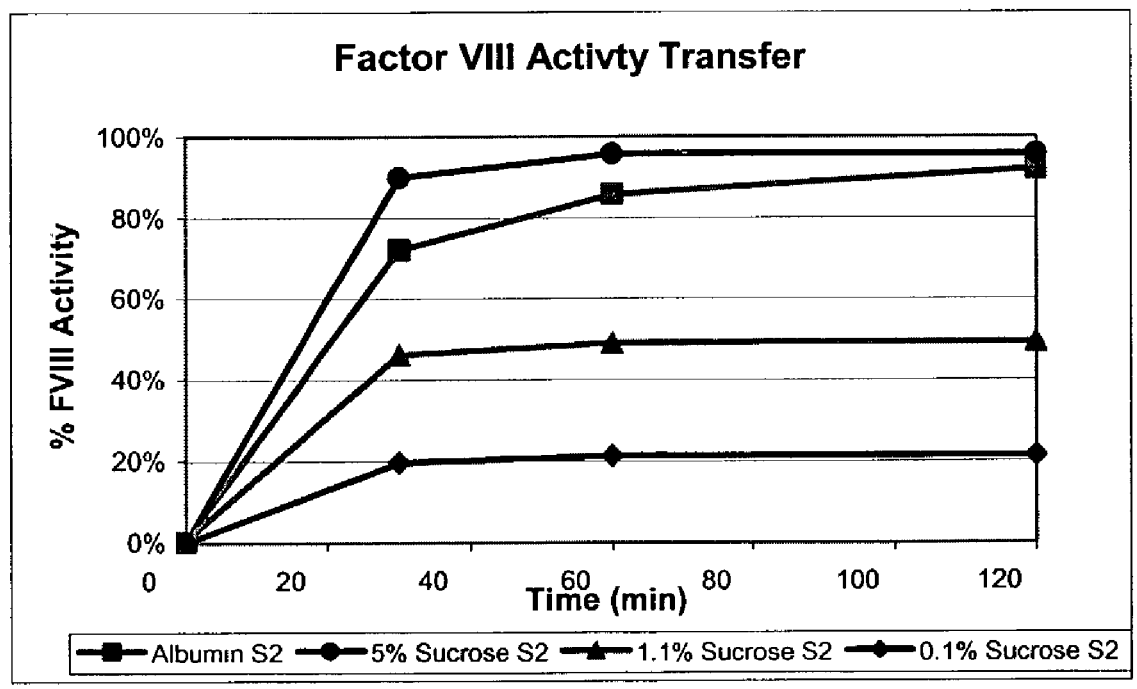
FIG. 12 is a graph showing the level of transfer of rFVIII activity from S1 to S2 throughout a membrane-based electrophoresis separation. Three differing concentrations of sucrose and one concentration of albumin were tested as stabilizing agents. The optimal stabilizer was 5% sucrose, which helped retain much more activity than the two lesser concentrations of sucrose.

When using 10 mg/mL HSA (1% w/v) as a stabilizing agent, rFVIII activity could be maintained and transferred in the electrophoresis apparatus from S1 to S2 with very little loss of activity. The rFVIII product, which was transferred to S2, was harvested at 30, 60 and 120 minutes so that the rFVIII in this stream was less exposed to the rigors of continuously passing through the electrophoresis apparatus. An average of 92% of the starting activity could be transferred from S1 and collected in S2 (FIG. 12).

Figure 13:
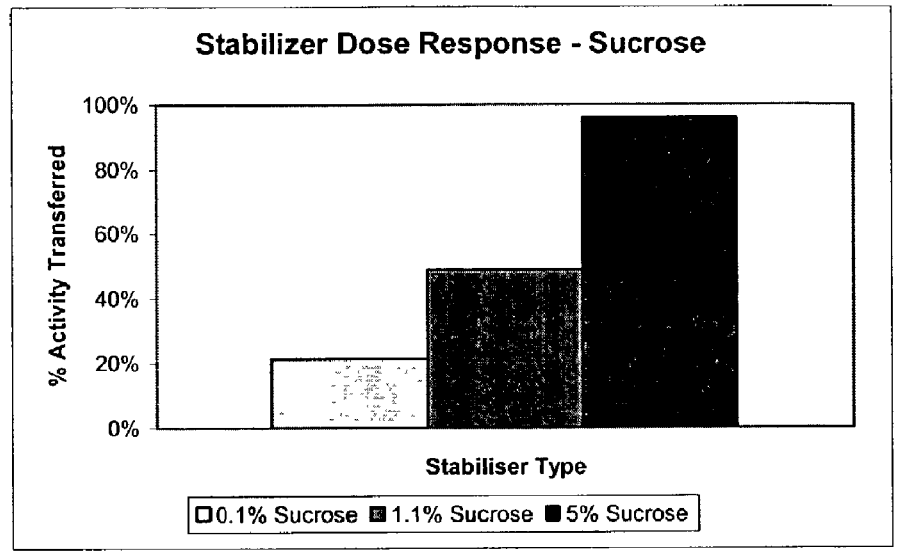
FIG. 13 is a graph showing the final recoveries of rFVIII activity from S2 of the membrane-based electrophoresis apparatus when the three combinations of stabilizer were used are shown above. The 5% sucrose stabilizer proved much better than the lower sucrose concentrations.

When sucrose was employed as the stabilizing agent, it was found that 0.11% sucrose maintained rFVIII activity better than no stabilizer. A large amount of activity, however, was still lost. If this level was then increased to 1.1%, greater activity recoveries are possible. The 1.1% sucrose concentration did not stabilize the rFVIII as well as the albumin. Due to the dose response seen with the sucrose concentration for 0.1% and 1.1%, a 5% concentration of sucrose was utilized (FIG. 13). When 5% sucrose was used as the stabilizing agent, the retention of activity was better than that seen with albumin. Using the higher concentration of sucrose enabled 96% of rFVIII activity to be transferred from S1 to S2 in 60 minutes.

The bottled sucrose-stabilized rFVIII product contained only 1.1% sucrose, as at higher levels it is likely to be detrimental to a patient. Sucrose at 1.1% was not found to stabilize rFVIII adequately during separation using an electrophoresis apparatus so a higher concentration was needed. This higher concentration of sucrose used during separation of FVIII may be reduced at the end of the purification scheme.

A purification scheme for rFVIII from cell culture supernatant was developed and mimics rFVIII expressed from CHO cells in culture. Equal parts cell culture supernatant and 10% sucrose were combined to produce a suitable starting material and rFVIII was spiked into this supernatant to produce approximately a 10 IU/mL concentration.

Figure 14:
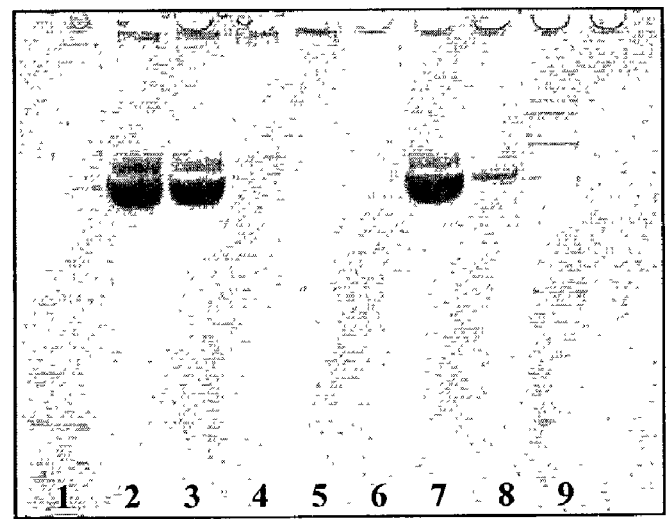
FIG. 14 is a SDS PAGE gel showing the starting material and end product in the rFVIII purification procedure using a membrane-based electrophoresis apparatus. Lane 5 contains the purified rFVIII product, which is completely free of albumin and transferrin and other low molecular weight contaminants. Lanes 7 and 8 contain the contaminants, which were removed from S1.

The purification scheme used pH 6.5 MES/histidine buffer with 5% sucrose. A ~500 kDa separation membrane was used to enable a size separation where the large rFVIII molecule (265 kDa) was retained in S1 while all of the smaller proteins such as albumin and transferrin were transferred to S2. The higher levels of sucrose (5%) helped to maintain rFVIII activity while almost all of the contaminating proteins were removed (FIG. 14). At 30 minutes, when a majority of the contaminants had been removed, 79% of activity remained. At 60 minutes, a more pure product was obtained having retained at least 65% of biological activity (FIG. 15).

Figure 15:
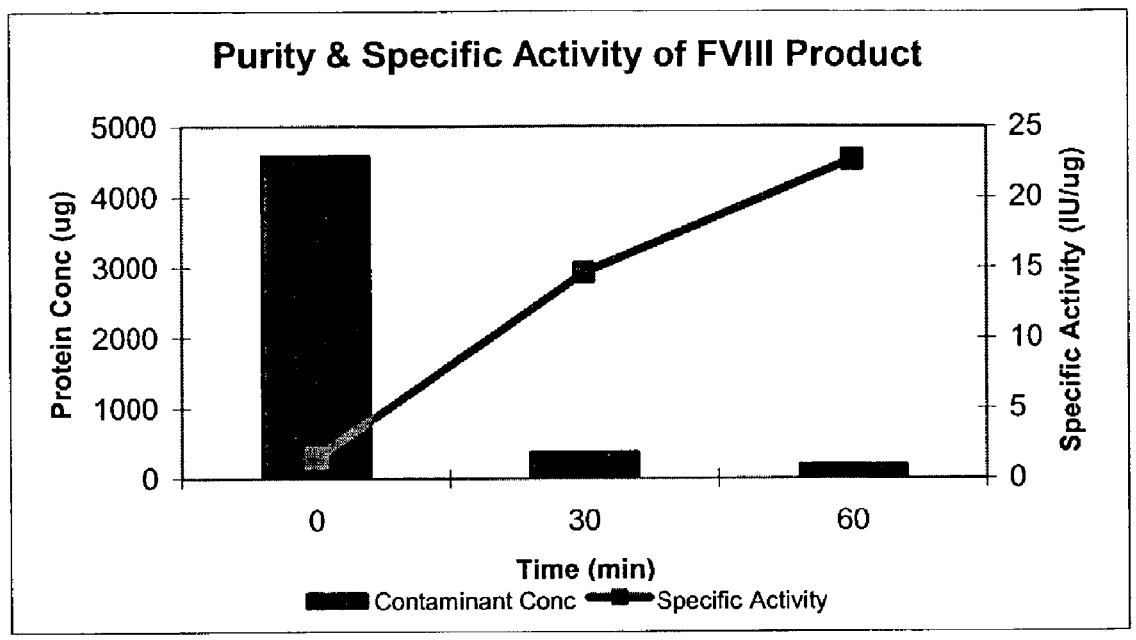
FIG. 15 is a graph of protein concentration vs. time in a membrane-based electrophoresis separation. As the level of impurities is reduced during the separation, a substantial increase in FVIII specific activity is observed.

The SDS PAGE gel separation shown in FIG. 15 shows that almost all of the contaminants were transferred from the protein-rich cell culture media present in S1 at the start of the run, to S2, while the activity assay proves that rFVIII remained in S1 (FIG. 14). The final product, which can be seen as Lane 5 on the polyacrylamide gel, contained only one protein band, which is at the very top of the gel.

The rFVIII-spiked cell culture supernatant contained 390 µg/mL of protein, as measured by Bradford total protein assay, and after purification using the electrophoresis method according to the present invention, the final product contained only 16 µg/mL of protein. As the product became more purified, the specific activity, measured as IU/µg of total protein, increased dramatically (FIG. 15). Greater than 96% of impurities were removed to S2, leaving recombinant FVIII purified in S1. This was analyzed using Coomassie stained SDS PAGE.

This purification process is further improved upon in a number of ways. In order to achieve purification and viral clearance in one step, transfer of the rFVIII across a separation membrane to give partitioning from any bioburden is effected by using a large pore size membrane as the separation and a ~500 kDa membrane as the second restriction membrane. This would allow rFVIII molecules to be moved away from all large molecular weight protein contaminants as well as virus and prion, while all of the lower molecular weight proteins which transfer with the rFVIII will be further moved into the buffer stream via the ~500 kDa restriction membrane. Further efforts in optimizing buffer pH and composition are readily known in the art and should also improve the stability of the rFVIII molecule while being purified.

Sucrose was found to be an excellent non-proteinaceous stabilizer for rFVIII according to the present methods. Sucrose produced a dose response in that the higher the concentration used, the better the activity retention. Concentrations of 0.1, 1.1, and 5% sucrose were tested, with the 5% sucrose concentration producing the best stabilizing effect for rFVIII.

Furthermore, electrophoresis methods according to the present claims have shown to be an excellent tool to purify rFVIII from cell culture supernatant. Greater than 96% of impurities were removed from cell culture supernatant with good retention of FVIII activity. The specific activity of the rFVIII product was found to increase considerably during purification, and SDS PAGE showed the product to be of single band purity. The whole separation was fast with the final product being produced in 60 minutes, preventing the highly unstable rFVIII molecule from losing significant functionality.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia before the priority date of each claim of this application.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A method for isolating Factor VIII (FVIII) from a sample containing FVIII and unwanted molecules comprising:
- (a) introducing the sample into a first interstitial volume of a solvent at a pH between about 6.5 and about 7.0 in an electrophoresis apparatus comprising
  - a separation membrane having a defined pore size with a molecular mass cut off different from the molecular mass of FVIII,
  - a first restriction membrane disposed between a first electrode zone and the separation membrane so as to define the first interstitial volume therebetween, and
  - a second restriction membrane disposed between a second electrode zone and the separation membrane so as to define a second interstitial volume therebetween;
- (b) adding one or more stabilizing agents to one or more of the sample, the first interstitial volume or the second interstitial volume, wherein the one or more stabilizing agents is present at a concentration of between about 2 g/L and about 50 g/L;
- (c) applying an electric potential between the first and second interstitial volumes such that the FVIII is located on one side of the separation membrane and the unwanted molecules are substantially located on the other side of the separation membrane; and
- (d) maintaining step (c) until a desired amount of the FVIII is isolated.

2. A method for isolating Factor VIII (FVIII) from a sample containing FVIII and unwanted molecules comprising:
- (a) introducing the sample into a first interstitial volume of a solvent at a pH between about 6.5 and about 7.0 in an electrophoresis apparatus comprising
  - a separation membrane having a defined pore size with a molecular mass cut off greater than the molecular mass of FVIII,
  - a first restriction membrane disposed between a first electrode zone and the separation membrane so as to define the first interstitial volume therebetween, and
  - a second restriction membrane disposed between a second electrode zone and the separation membrane so as to define a second interstitial volume therebetween;
- (b) adding one or more stabilizing agents to either or both of the sample and the second interstitial volume, wherein the one or more stabilizing agents is present at a concentration of between about 2 g/L and about 50 g/L;
- (c) applying an electric potential between the first and second interstitial volumes causing movement of the FVIII in the first interstitial volume through the separation membrane into the second interstitial volume while the unwanted molecules are substantially prevented from entering the second interstitial volume; and
- (d) maintaining step (c) until a desired amount of the FVIII is moved to the second interstitial volume.

3. A method for isolating Factor VIII (FVIII) from a sample containing FVIII and unwanted molecules comprising:
- (a) introducing the sample into a first interstitial volume of a solvent at a pH between about 6.5 and about 7.0 in an electrophoresis apparatus comprising
  - a separation membrane having a defined pore size with a molecular mass cut off less than the molecular mass of FVIII,
  - a first restriction membrane disposed between a first electrode zone and the separation membrane so as to define the first interstitial volume therebetween, and
  - a second restriction membrane disposed between a second electrode zone and the separation membrane so as to define a second interstitial volume therebetween;
- (b) adding one or more stabilizing agents to either or both of the sample and the second interstitial volume, wherein the one or more stabilizing agents is present at a concentration of between about 2 g/L and about 50 g/L;

(c) applying an electric potential between the first and second interstitial volumes causing movement of the unwanted molecules in the sample in the first interstitial volume through the separation membrane into the second interstitial volume while the FVIII is substantially prevented from entering the second interstitial volume and is retained in the first interstitial volume; and (d) maintaining step (c) until a desired amount of the unwanted molecules in the sample are removed from the first interstitial volume.

4. The method according to claim 1, 2 or 3 wherein the sample is plasma or a fraction thereof, a cryoprecipitate or a fraction thereof, a source of recombinant FVIII, or combinations or mixtures thereof.

5. The method according to claim 1, 2 or 3 wherein the one or more stabilizing agents is a buffering component, a molarity altering component, a protein, an amino acid or a sugar.

6. The method according to claim 1, 2 or 3 wherein the one or more stabilizing agents is selected from the group consisting of sorbitol, salt, glycerol, sucrose, lactose, dextran/dextrose, glycine, gelatin, potassium acetate, azide, and protease inhibitors.

7. The method according to claim 5 wherein the one or more stabilizing agents agent is albumin, a mixture of amino acids, sucrose, or a mixture thereof.

8. The method according to claim 7 wherein the albumin is present at a concentration of at least about 2 mg/mL (2 g/L) the mixture of amino acids is present at a concentration of at least about 0.01 g/mL (10 g/L), and the sucrose is present at a concentration of at least about 1% (10 g/L).

9. The method according to claim 7 wherein the albumin is present at a concentration of about 10 mg/mL (10 g/L), the mixture of amino acids is present at a concentration of about 0.05 g/mL (50 g/L), and the sucrose is present at a concentration of about 5% (50 g/L).

10. The method according to claim 1, 2 or 3 wherein in step (a), the solvent comprises a buffer such that the FVIII has a net negative charge.

11. The method according to claim 10 wherein the buffer is MES/Histidine at a pH of 6.5, the separation membrane has a molecular mass cut off of about 1500 kDa and the first and second restriction membranes have a molecular mass cut off of about 5 kDa.

12. The method according to claim 1, 2 or 3 wherein the FVIII obtained in step (d) retains at least about 40% specific activity.

13. The method according to claim 12 wherein the FVIII retains at least about 60% specific activity.

14. The method according to claim 13 wherein the FVIII retains greater than about 75% specific activity.

15. The method according to claim 1, 2, or 3 wherein the sample is a cell supernatant or cell lysate containing a recombinant (rFVIII).

16. A method for separating at least one toxin, pathogen or infectious agent contaminant from a sample containing FVIII comprising:

(a) introducing the sample containing the FVIII and the at least one toxin, pathogen or infectious agent contaminant into a first interstitial volume of a solvent at a pH between about 6.5 and about 7.0 in an electrophoresis apparatus comprising a separation membrane having a defined pore size with a molecular mass cut off greater than the molecular mass of FVIII, a first restriction membrane disposed between a first electrode zone and the separation membrane so as to define the first interstitial volume therebetween, and a second restriction membrane disposed between a second electrode zone and the separation membrane so as to define a second interstitial volume therebetween;

(b) adding one or more stabilizing agents to either or both of the sample and the second interstitial volume, wherein the one or more stabilizing agents is present at a concentration of between about 2 g/L and about 50 g/L;

(c) applying an electric potential between the first and second interstitial volumes causing movement of the FVIII in the first interstitial volume through the separation membrane into the second interstitial volume while unwanted molecules that include the at least one toxin, pathogen or infectious agent contaminant are prevented from entering the second interstitial volume; and (d) maintaining step (c) until a desired amount of the FVIII is moved to the second interstitial volume.

17. A method for separating at least one toxin, pathogen or infectious agent contaminant from a sample containing FVIII, comprising:

(a) introducing the sample containing the FVIII and the at least one toxin, pathogen or infectious agent contaminant into a first interstitial volume of a solvent at a pH between about 6.5 and about 7.0 in a first electrophoresis apparatus comprising a first separation membrane having a defined pore size with a molecular mass cut off greater than the molecular mass of FVIII, a first restriction membrane disposed between a first electrode zone and the first separation membrane so as to define the first interstitial volume therebetween, and a second restriction membrane disposed between a second electrode zone and the first separation membrane so as to define a second interstitial volume therebetween;

(b) adding one or more stabilizing agents to either or both of the sample and the second interstitial volume, wherein the one or more stabilizing agents is present at a concentration of between about 2 g/L and about 50 g/L;

(c) applying an electric potential between the first and second interstitial volumes causing movement of the FVIII in the first interstitial volume through the first separation membrane into the second interstitial volume while unwanted molecules that include the at least one toxin, pathogen or infectious agent contaminant are prevented from entering the second interstitial volume;

(d) maintaining step (c) until a desired amount of the FVIII is moved to the second interstitial volume;

(e) adding the FVIII obtained from step (d) into a third interstitial volume of a solvent at a pH between about 6.5 and about 7.0 in a second electrophoresis apparatus comprising a second separation membrane having a defined pore size with a molecular mass cut off greater than that of FVIII, a third restriction membrane disposed between a third electrode zone and the second separation membrane so as to define the third interstitial volume therebetween, and a fourth restriction membrane disposed between a fourth electrode zone and the second separation membrane so as to define a fourth interstitial volume therebetween;

(f) applying an electric potential between the third and fourth interstitial volumes causing movement of the FVIII in the third interstitial volume through the second separation membrane into the fourth interstitial volume while unwanted molecules that include the at least one toxin, pathogen or infectious agent contaminant are prevented from entering the fourth interstitial volume; and (g) maintaining step (f) until a desired amount of the FVIII is moved to the fourth interstitial volume.

18. A method for separating at least one toxin, pathogen or infectious agent contaminant from a sample containing FVIII, comprising:

(a) introducing the sample containing the FVIII and the at least one toxin, pathogen or infectious agent contaminant into a first interstitial volume of a solvent at a pH between about 6.5 and about 7.0 in a first electrophoresis apparatus comprising
a first separation membrane having a defined pore size with a molecular mass cut off less than the molecular mass of FVIII,
a first restriction membrane disposed between a first electrode zone and the first separation membrane so as to define the first interstitial volume therebetween, and
a second restriction membrane disposed between a second electrode zone and the first separation membrane so as to define a second interstitial volume therebetween;

(b) adding one or more stabilizing agents to either or both of the sample and the second interstitial volume, wherein the one or more stabilizing agents is present at a concentration of between about 2 g/L and about 50 g/L;

(c) applying an electric potential between the first and second interstitial volumes causing movement of unwanted molecules that include the at least one toxin, pathogen or infectious agent contaminant in the first interstitial volume through the first separation membrane into the second interstitial volume while the FVIII is prevented from entering the second interstitial volume and is retained in the first interstitial volume;

(d) maintaining step (c) until a desired amount of the unwanted molecules in the sample are removed from the first interstitial volume;

(e) adding the FVIII obtained from step (d) into a third interstitial volume of a solvent at a pH between about 6.5 and about 7.0 in a second electrophoresis apparatus comprising
a second separation membrane having a defined pore size with a molecular mass cut off greater than that of FVIII,
a third restriction membrane disposed between a third electrode zone and the second separation membrane so as to define the third interstitial volume therebetween, and
a fourth restriction membrane disposed between a fourth electrode zone and the second separation membrane so as to define a fourth interstitial volume therebetween;

(f) applying an electric potential between the third and fourth interstitial volumes causing movement of the FVIII in the third interstitial volume through the second separation membrane into the fourth interstitial volume while unwanted molecules that include the at least one toxin, pathogen or infectious agent contaminant are prevented from entering the fourth interstitial volume; and (g) maintaining step (f) until a desired amount of the FVIII is moved to the fourth interstitial volume.

19. A method for separating at least one toxin, pathogen or infectious agent contaminant from a sample containing FVIII, comprising:

(a) adding the sample containing the FVIII and the at least one toxin, pathogen or infectious agent contaminant into a first interstitial volume of a solvent at a pH between about 6.5 and about 7.0 in a first electrophoresis apparatus comprising
a first separation membrane having a defined pore size with a molecular mass cut off greater than the molecular mass of FVIII,
a first restriction membrane disposed between a first electrode zone and the first separation membrane so as to define the first interstitial volume therebetween, and
a second restriction membrane disposed between a second electrode zone and the first separation membrane so as to define a second interstitial volume therebetween;

(b) adding one or more stabilizing agents to either or both of the sample and the second interstitial volume, wherein the one or more stabilizing agents is present at a concentration of between about 2 g/L and about 50 g/L;

(c) applying an electric potential between the first and second interstitial volumes causing movement of the FVIII in the first interstitial volume through the first separation membrane into the second interstitial volume while unwanted molecules that include the at least one toxin, pathogen or infectious agent contaminant are substantially prevented from entering the second interstitial volume;

(d) maintaining step (c) until a desired amount of the FVIII is moved to the second interstitial volume;

(e) adding the FVIII obtained from step (d) into a third interstitial volume of a solvent at a pH between about 6.5 and about 7.0 in a second electrophoresis apparatus comprising
a second separation membrane having a defined pore size with a molecular mass cut off greater than the at least one toxin, pathogen or infectious agent contaminant,
a third restriction membrane disposed between a third electrode zone and the second separation membrane so as to define the third interstitial volume therebetween, and
a fourth restriction membrane disposed between a fourth electrode zone and the second separation membrane so as to define a fourth interstitial volume therebetween;

(f) applying an electric potential between the third and fourth interstitial volumes causing movement of the at least one toxin, pathogen or infectious agent contaminant in the third interstitial volume through the second separation membrane into the fourth interstitial volume while the FVIII is prevented from entering the fourth interstitial volume; and (g) maintaining step (f) until a desired amount of the FVIII is in the third interstitial volume.

20. A method for obtaining FVIII substantially free from at least one toxin, pathogen or infectious agent contaminant comprising:
- (a) introducing a sample containing the FVIII and at least one toxin, pathogen or infectious agent contaminant into a first interstitial volume of a solvent at a pH between about 6.5 and about 7.0 in a first electrophoresis apparatus comprising
  - a first separation membrane having a defined pore size with a molecular mass cut off less than the molecular mass of FVIII,
  - a first restriction membrane disposed between a first electrode zone and the first separation membrane so as to define the first interstitial volume therebetween, and
  - a second restriction membrane disposed between a second electrode zone and the first separation membrane so as to define a second interstitial volume therebetween;
- (b) adding one or more stabilizing agents to either or both of the sample and the second interstitial volume, wherein the one or more stabilizing agents is present at a concentration of between about 2 g/L and about 50 g/L;
- (c) applying an electric potential between the first and second interstitial volumes causing movement of unwanted molecules that include the at least one toxin pathogen or infectious agent contaminant in the sample in the first interstitial volume through the first separation membrane into the second interstitial volume while the FVIII is substantially prevented from entering the second interstitial volume and is retained in the first interstitial volume;
- (d) maintaining step (c) until a desired amount of the unwanted molecules in the sample are removed from the first interstitial volume;
- (e) adding the FVIII obtained from step (d) and containing at least one toxin, pathogen or infectious agent contaminant into a third interstitial volume of a solvent at a pH such that the at least one toxin, pathogen, infectious agent contaminant has a desired charge state in a second electrophoresis apparatus comprising
  - a second separation membrane having a defined pore size with a molecular mass cut off greater than the at least one toxin, pathogen or infectious agent contaminant,
  - a third restriction membrane disposed between a third electrode zone and the separation membrane so as to define the third interstitial volume therebetween, and
  - a fourth restriction membrane disposed between a fourth electrode zone and the second separation membrane so as to define a fourth interstitial volume therebetween;
- (f) applying an electric potential between the third and fourth interstitial volumes causing movement of the at least one toxin, pathogen or infectious agent contaminant in the third interstitial volume through the second separation membrane into the fourth interstitial volume while the FVIII is prevented from entering the fourth interstitial volume; and
- (g) maintaining step (f) until a desired amount of the FVIII is in the third interstitial volume.

21. The method according to claim 16, 17, 18, 19, or 20 wherein the at least one toxin, pathogen or infectious agent contaminant is selected from the group consisting of endotoxins, prions, viruses, bacteria, fungi, yeasts and protozoa.

22. The method according to claim 16, 17, 18, 19, or 20 wherein the pathogen or infectious agent contaminant is a virus.

* * * * *